US 6,330,299 B1

(12) United States Patent
Curtis et al.

(10) Patent No.: US 6,330,299 B1
(45) Date of Patent: Dec. 11, 2001

(54) SYSTEM AND METHOD FOR DETERMINING DOSE AREA PRODUCT IN AN X-RAY IMAGING SYSTEM

(75) Inventors: Steven Emerson Curtis, Salt Lake City; Richard Larry Anderton, West Jordan; Steven James Brown, West Valley City; David Ellis Barker, Salt Lake City; Matthew Scott Curtis, Provo, all of UT (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/591,418

(22) Filed: Jun. 10, 2000

(51) Int. Cl.[7] .................................................. G01N 23/04
(52) U.S. Cl. ............................................ 378/62; 378/108
(58) Field of Search ................................... 378/62, 98, 108

(56) References Cited

U.S. PATENT DOCUMENTS 5,694,449  12/1997 Aragones ............................ 378/115
5,798,528 * 8/1998 Butsch et al. ..................... 250/492.2

* cited by examiner

*Primary Examiner*—David V. Bruce
(74) *Attorney, Agent, or Firm*—McAndrews, Held & Malloy, Ltd.; Peter J. Vogel; Michael A. Dellapenna

(57) ABSTRACT

A system an method for determining the Dose Area Product (DAP) in an X-ray imaging system is provided. The present system constructs a pre-determined parameter space describing the DAP contour over ranges of typical imaging parameters. Later, when the employed in clinical imaging, a DAP processor on board the imaging system received a set of the imaging parameters being employed. The DAP applies the set of parameters to the parameter space to interpolate the DAP being delivered by the clinical imaging system. The present system may be individually calibrated to a specific X-ray imaging system to provide more optimal DAP values. Additionally, in imaging system employing an asymmetric shutter, such as a one-leaf shutter, the present system may determine a rotational scale factor for the DAP based on the rotation of the shutter. The rotational scale factor may also be calibrated to an individual X-ray imaging system.

18 Claims, 6 Drawing Sheets

400

APPROXIMATE INTENSITY IN PERCENT
(CALLING THE CENTER OF THE BEAM 100%)

DEGREES ROTATION

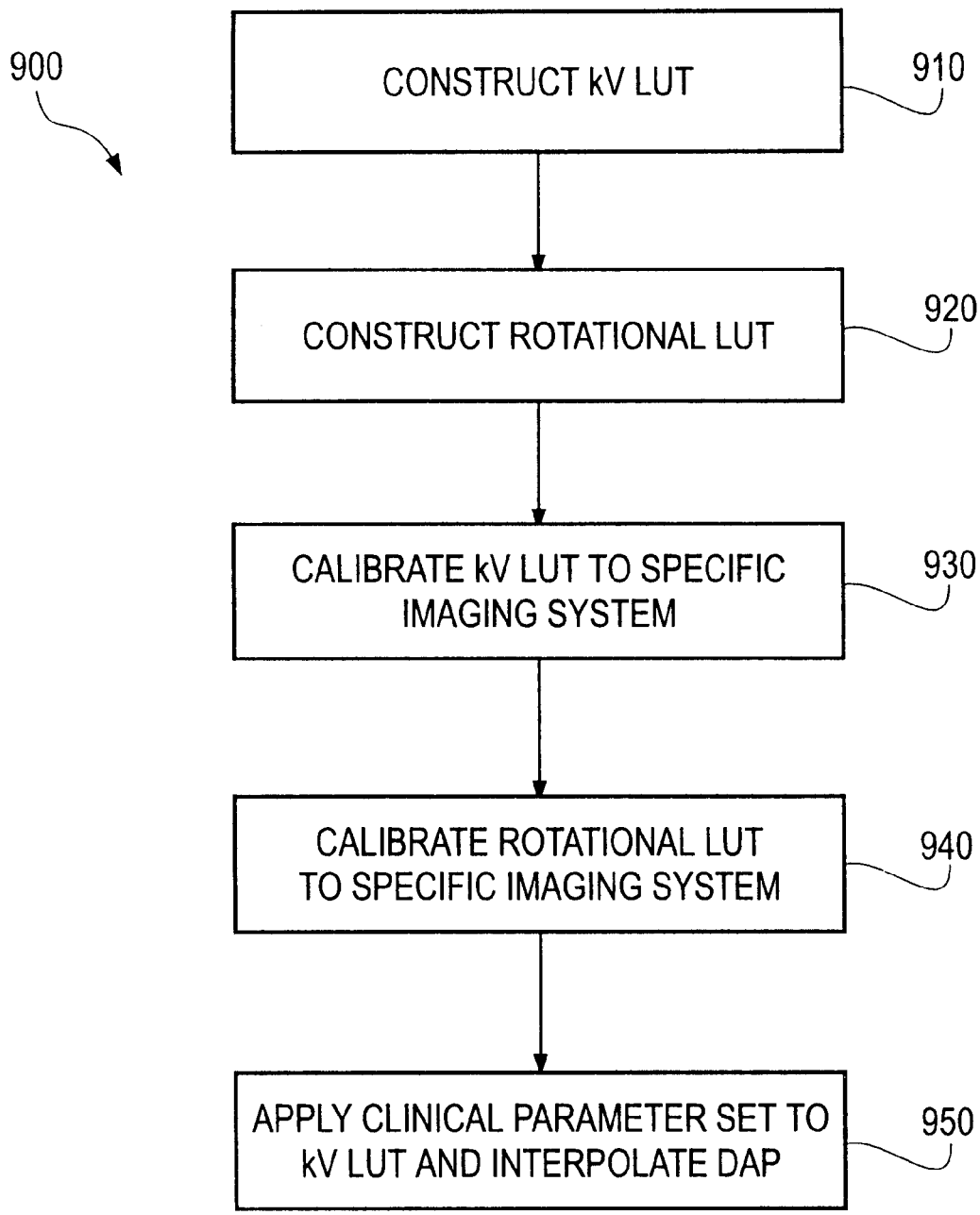

SYSTEM AND METHOD FOR DETERMINING DOSE AREA PRODUCT IN AN X-RAY IMAGING SYSTEM

BACKGROUND OF THE INVENTION

The present invention generally relates to determining the Dose Area product (DAP) in an X-ray imaging system. In particular, the present invention relates to system for allowing the determination of DAP during clinical imaging without direct measurement or additional equipment.

It has long been recognized that the amount of X-ray radiation a patient is exposed to during imaging should be minimized, due to the potential ill effects possible through over exposure of the patient to X-ray radiation. In order to quantitize the amount of X-ray radiation that the patient has been exposed to, some system for measuring the dose of X-ray radiation received by the patient is needed.

Because of several factors, such as the varying contour of a patient's skin surface and even the uncertainty of the average distance from the patient to X-ray source, it is often difficult to determine the patient's actual dose of X-ray radiation. Consequently, instead of measuring the patient's actual dose of X-ray radiation, a different parameter, called the Dose Area product (DAP) is measured. The DAP is a measurement of the surface dose obtained by multiplying the dose at a given distance by the area being radiated. The DAP is consequently a measurement of the emitted X-ray radiation, rather than a measurement of the dose absorbed by the patient. However, the DAP is a good approximation of the dose the patient has received. The DAP is an important clinical tool because the DAP provides an indication of the radiation that a patient is receiving for a given procedure, which allows the doctor to monitor and adjust the dose while maintaining image quality.

The DAP thus eliminates much of the uncertainty inherent in attempting to ascertain the patient's actual skin dose. For example, the cumulative radiation dose at a surface is inversely proportional to the square of the distance between the surface and the X-ray source. Additionally, the area being imaged is directly proportional to the square of the distance between the surface and the X-ray source. Consequently, determining the DAP, the product of the dose and area, yields a parameter that is independent of source to imaging surface distance. The DAP provides an obtainable figure of merit to gauge the X-ray radiation received by a patient at any distance from the emitter.

In the past, some X-ray imaging systems have collected the necessary data for determining the DAP by inserting a measuring device in the immediate vicinity of the X-ray source and exposing the measuring device to the X-ray source during imaging. The measuring device is typically a gas-filled ionization chamber and associated electronic instrumentation and is designed to yield dose measurements or DAP measurements. Locating the ion chamber in proximity to and exposed to the X-ray source has been the only reasonable choice, since the ionization chamber must be larger than the entire X-ray source but must also not be in the way of the patient.

Because the DAP is independent of distance to the X-ray emitter, the DAP obtained by the instrumentation gives an indication of DAP anywhere along the trajectory of the X-ray beam (including at the location of the patient's skin surface). However, very close to the X-ray source, where the ion chamber is located, the X-ray beam typically includes off-axis scatter components that do not engage the patient. Additionally, the patient may generate secondary backscatter X-rays. Additional X-ray radiation from off-axis scattering or back scattered X-rays may contribute to a misleading DAP measurement. Additionally, erroneous scattering values may vary widely and in a complex way with, for example, X-ray kV settings and other conditions.

The use of the ion chamber to determine DAP during imaging is not optimal for a variety of reasons. The ion chamber and its associated instrumentation are expensive. Also, the expense of the ion chamber is multiplied because an ion chamber must be installed on each X-ray imaging system. Additionally, servicing the ion chamber may require expensive system downtime. The ion chamber and its associated instrumentation may also need to be re-calibrated often. In the case of mobile X-ray imaging systems rather than large, fixed-room systems especially, cost is of particular concern Consequently, a need exists for a system to calculate the DAP without the additional expense of additional imaging system components. Preferably, such a system would provide for minimizing the downtime of the imaging system and provide for easy re-calibration. Also, such a system preferably minimizes additional imaging components to minimize system complexity.

BRIEF SUMMARY OF THE INVENTION

A preferred embodiment of the present invention provides a system and method for determining the Dose Area product (DAP) in an X-ray imaging system. A parameter space describing the contour of the DAP over ranges of typical imaging parameters is first constructed. The parameter space may be calibrated to an individual imaging system. If the individual imaging system employs an asymmetric shutter, a rotational correction value corresponding the shutter may be determined. The rotational correction value may also be calibrated to the individual imaging system. During clinical use, the set of imaging parameters being used is applied to the parameter space and the DAP for the current imaging process is interpolated. If the imaging system employs an asymmetric shutter, the rotational correction value is applied to the DAP to deliver a more optimal DAP value.

BRIEF DESCRIPTION OF THE DRAWINGS

FIG. 9 illustrates a flowchart providing a lower-level view of the system for determining the DAP during clinical imaging of FIG. 7.

DETAILED DESCRIPTION OF THE INVENTION

Figure 1:
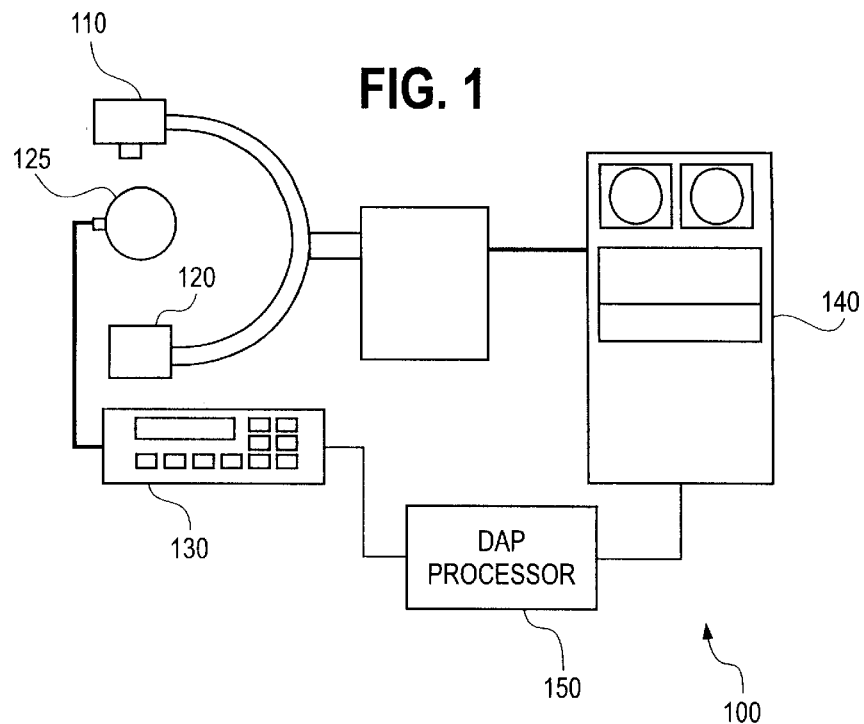
FIG. 1 illustrates a system for determining a Dose Area product (DAP) in an X-ray imaging system according to a preferred embodiment of the present invention.

FIG. 1 illustrates a system 100 for determining a Dose Area Product (DAP) in an X-ray imaging system according to a preferred embodiment of the present invention. The system 100 includes a an X-ray emitter 110, an X-ray receiver 120, an ion chamber 125, a dosimeter 130, a system computer 140, and a DAP processor 150. The X-ray emitter 110 and X-ray receiver 120 are typically coupled to and controlled from the system computer 140. The ion chamber 125 is coupled to the dosimeter 130 and allows the dosimeter to determine the dose of X rays emitted from the emitter 110.

The DAP processor 150 is coupled to both the system computer 140 and the dosimeter 130 and receives data from both. The DAP processor 150 receives X-ray dose data from the dosimeter 130 and receives data regarding configuration parameters of the X-ray emitter 110 from the system computer 140.

As further described below, the DAP processor 150 determines the DAP for a certain set of system parameters. As further described below, the DAP processor 150 then constructs a parameter space for the DAP based on the system parameters. During clinical use of the imaging system, the DAP processor 150 determines the DAP directly, without the use of concurrent measurement, by interpolating the current imaging parameters into the constructed parameter space.

The X-ray emitter 110 and X-ray receiver 120 typically are components in a medical X-ray imaging system. When the X-ray emitter 110 and x ray receiver 120 are used to image a patient, the patient is placed between the emitter 110 and the receiver 120. The emitter 110 is then energized, typically by an external controller, such as a controller based in the system computer 140. The emitter 110 emits X-rays which pass through the collimator 115, through the patient and are received by the X-ray receiver 120. The X-ray receiver 120 interprets the intensity of the received X-rays to produce an X-ray image of the patient. The X-ray emitter 110 typically includes a semi-transparent shutter and an iris as further discussed below. The shutter and the iris are typically adjustable and are externally controlled from the system computer 140 as further discussed below.

Figure 2:
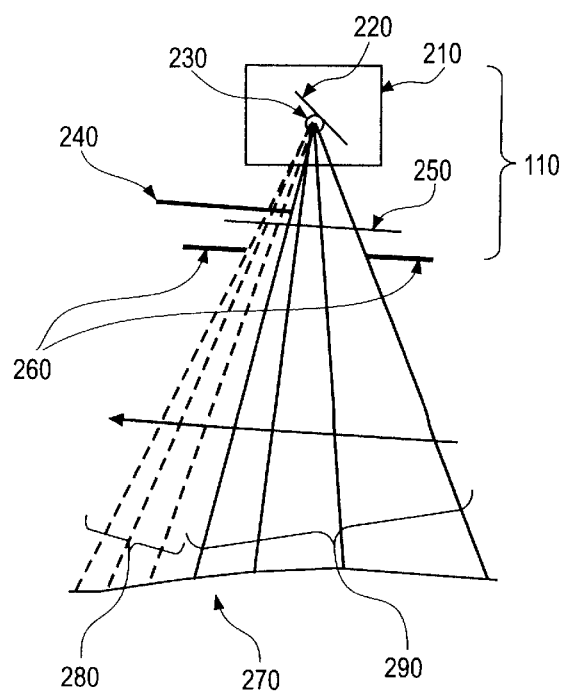
FIG. 2 illustrates a side view of the emitter of FIG. 1 in greater detail for use in a preferred embodiment of the present invention.

FIG. 2 illustrates a side view of the emitter 110 of FIG. 1 in greater detail. The emitter 110 includes an X-ray tube 210, an X-ray anode 220, an X-ray focal spot source 230, a semi-transparent shutter 240, an optional beam hardening metal filter 250, an iris 260, and a patient 270. Also shown is an X-ray beam having a partially attenuated region 280 and an unattenuated region 290. The X-ray anode 220 provides the originating surface for the X-rays in the form of the focal spot X-ray source 230. The intensity of the generated X-ray beam varies to a higher order power of the high voltage (kV) applied to the X-ray tube 210, and is directly proportional to the current (mA) through the X-ray tube 210.

In operation, X-rays generated in the X-ray tube 210 pass from the x ray anode 220 at the focal spot source 230 where the X-rays are directed toward the patient 270. The X-rays pass from the focal spot source 230 through the shutter 240 and the metal filter 250 (if used). Finally, the X-rays pass through the iris 260 and travel to the patient 270.

As shown in FIG. 2, a portion of the X-rays pass through the shutter 240. The shutter 240 is typically semi-transparent to the X-rays. Thus, the X-rays that pass through the shutter 240 are partially attenuated. Consequently, the shutter 240 may be used to spatially manipulate the X-ray intensity of the X-ray beam. Also, the positioning of the shutter 240 may have a large impact on system performance due to the heel effect (described below) and the shutter's position in the X-ray beam.

As shown in FIG. 2, the cross section dimensions of the X-ray beam available for imaging is limited by the iris 260. The iris 260 typically uses a heavy (x ray-blocking) metal such as lead or tungsten.

Many factors may impact the uniformity of the X-ray beam, and consequently, the reliability of any DAP determination. For example, because the surface of the anode 210 is at an angle compared to the exit plane of the X-rays emitted from the X-ray rube 210, the X-ray intensity is not uniform across the X-ray beam. In this example, the intensity is weaker on the right side of the X-ray beam, due to the orientation of the anode 220. The change in uniformity is illustrated by the arrow in FIG. 2 pointing to the left across the path of the X-ray beam. The lateral change in uniformity of the X-ray beam is known as the heel effect.

Figure 5:
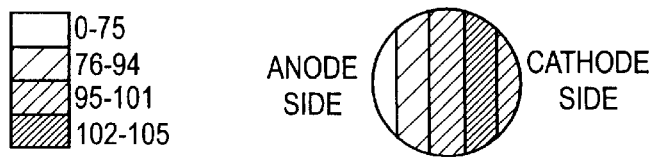
FIG. 5 illustrates the heel effect, that is, the variance in the intensity of the X-ray radiation across the X-ray beam.

FIG. 5 illustrates the heel effect, that is, the variance in the intensity of the X-ray radiation across the X-ray beam. As shown in FIG. 5, the intensity of the X-ray beam varies from as high as 105% to as low as 75% of the intensity of the X-ray beam at the center of the beam. The beam intensity also varies laterally, rather than radially across the X-ray beam.

In addition to heel effect, the X-ray intensity may be altered by the inherent filtration of the materials in the X-ray tube 210. After exiting the X-ray tube 210 the X-ray beam may also be filtered by other metal filtering 250 that is purposefully placed in the path of the beam.

Most relevantly, the adjustable shutter 240 also known as a shutter leaf or leaves, may be moved in and out of the path of the X-ray beam. Positioning the shutter 240 in the path of the X-ray beam produces significant attenuation of a portion of the X-ray beam. Conceptually, positioning the shutter 240 in the path of the X-ray beam partitions the X-ray beam into a partially attenuated region 280 and an unattenuated region 290. The shutter 240 may be any of several types including single leaf and dual leaf, for example. The shutter 240 may also be able to rotate around the central axis of the X-ray beam.

Figure 3:
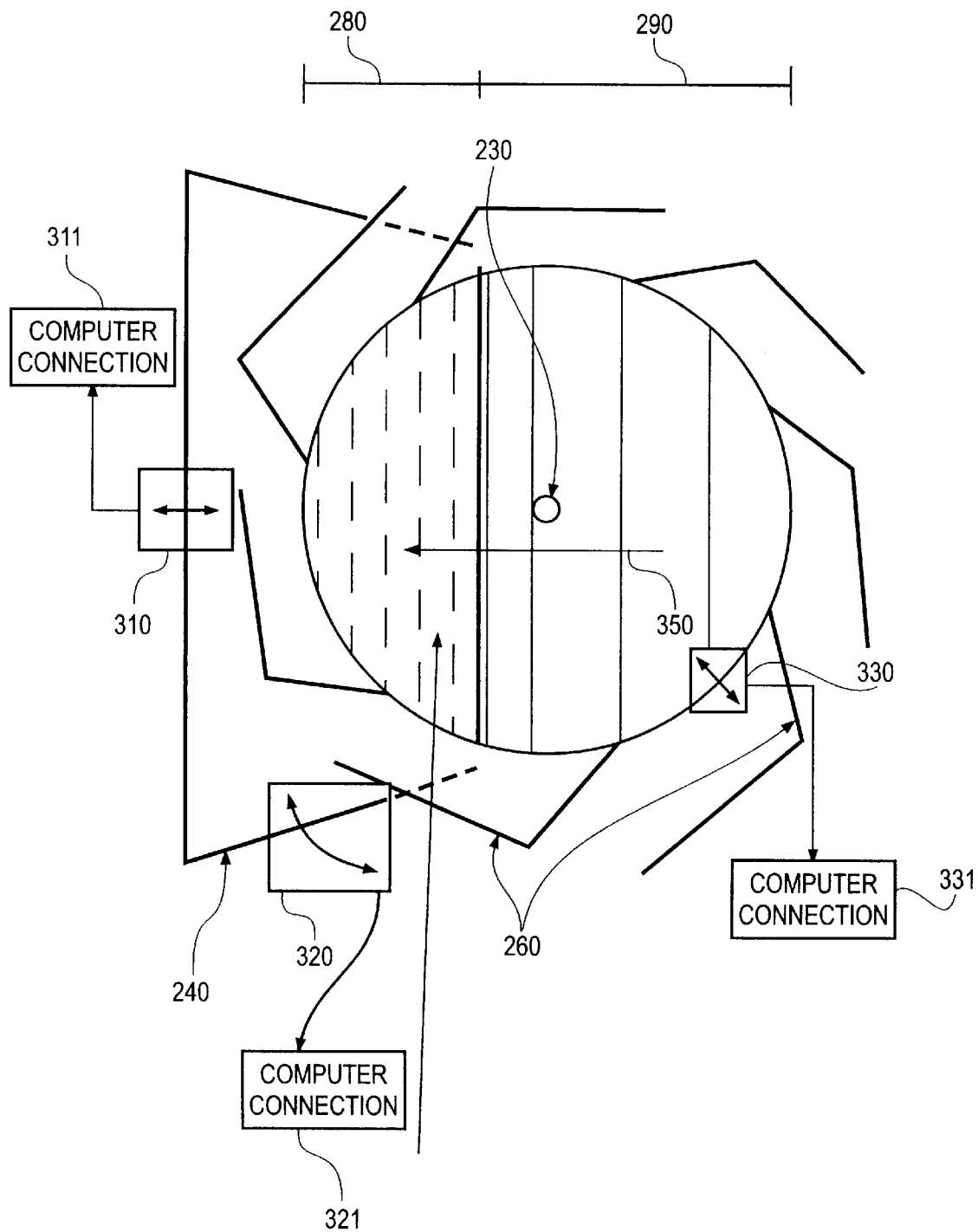
FIG. 3 illustrates the emitter of FIG. 1 as seen from below.

FIG. 3 illustrates the emitter 110 of FIG. 1 as seen from below and looking into the emitter 110. FIG. 3 includes the X-ray focal spot source 230, the shutter 240, the iris 260, a lateral shutter positioner 310 and its accompanying computer connection 311, a rotational shutter positioner 320 and its accompanying computer connection 321, an iris diameter controller 330 and its accompanying computer connection 331, the partially attenuated region 280, and the unattenuated region 290. The direction of the heel effect gradient is also indicated by an arrow 350.

The semi-transparent shutter 240 is shown oriented at zero degrees, that is, orthogonal to the direction of the heel effect gradient and on the side with the stronger X-ray intensity. In operation, the shutter 240 is laterally positioned by the lateral shutter positioner 310. The lateral position of the shutter 240 is relayed from the lateral shutter positioner 310 to the system computer 140 of FIG. 1 through the computer connection 311. The shutter 240 is rotationally positioned by the rotational shutter positioner 320. The rotational position of the shutter 240 is relayed from the rotational shutter positioner 320 to the system computer 140 of FIG. 1 through the computer connection 321. The diameter of the iris 260 of FIG. 3 is controlled by the iris diameter controller 330. The diameter of the iris 260 is relayed from the iris diameter controller 330 to the system computer 140 of FIG. 1 through the computer connection 331. The lateral and rotational position of the shutter 240 and the diameter of the iris are relayed from the system computer 140 to the DAP processor 150. The lateral and rotational position of the shutter 240 and the diameter of the iris 260 are important parameters in the determination of the DAP, as further described below.

The shutter of FIG. 3 employs only one shutter leaf, but, a multiple leaf shutter system such as dual shutter leaf system may be employed. In a dual shutter leaf system, the shutter leaves work together in harmony to occlude the X-ray beam on opposing sides of the central axis. The shutter leaf or leaves may be made of material that virtually blocks the X-ray beam, or that only partially blocks the beam, depending on the various imaging modalities. The shutter leaves may have an irregular shape and thickness, such as tapered blades. The shutter leaf shown in FIG. 3 is oriented at an angle defined as zero degrees. At this angle the shutter is blocking more X-ray intensity than at any other angle (for a constant lateral distance from the central axis passing through the focal spot X-ray source) because it is located in the path of the Xray beam that has the highest intensity due to the heel effect. If the shutter leaf were located on the opposite side then the position angle would be at the 180 degrees. Also, when the shutter is positioned at the 180 degree position angle, the shutter blocks less of the x-ray intensity than at any other angle due to the heel effect.

During clinical use, the X-ray beam intensity may vary in a complex way as a function of the several parameters. These parameters include the applied voltage in kV, the current passing through the X-ray tube in mA, the heel effect, inherent and other fixed filtration, and shutter leaf characteristics such as shape, irregular thickness, number of leaves, and position, for example. Additionally, the iris position determines the physical extent of the X-ray beam cross section and the iris may be worn and may yield additional variance in beam intensity.

A preferred embodiment of the present invention analyzes the variance of many of the above parameters to determine a system to provide the DAP directly, without additional dose measurements during clinical use. Positional data for the iris diameter, the shutter leaf distance from the central axis, and shutter leaf rotation relative to the direction of the heel effect attenuation may be monitored by the system computer, as indicated in FIG. 3. Typically, some imaging systems, such as higher performance mobile X-ray imaging systems, will already be monitoring these parameters for other reasons. Additionally, other parameters such as the kV and mA of the X-ray beam and the exposure time will also already be typically known by the system computer.

Figure 7:
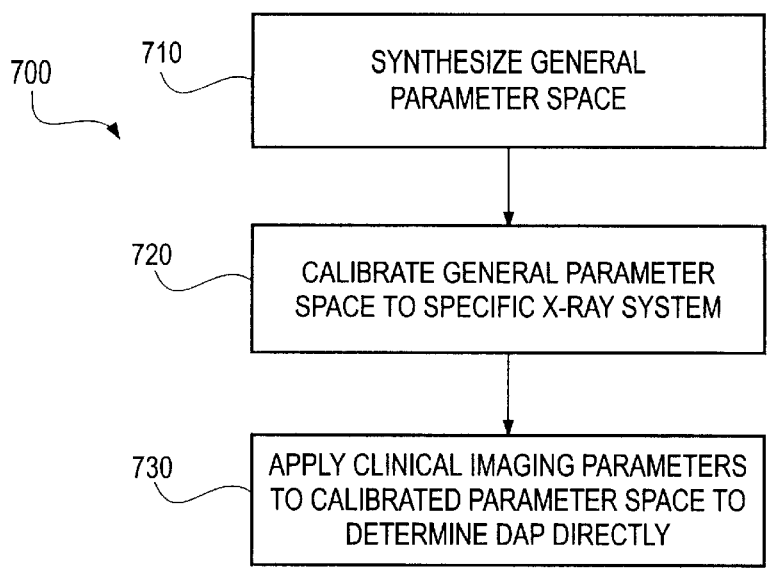
FIG. 7 illustrates a flowchart of high-level view of the system for determining the DAP during imaging according to a preferred embodiment of the present

FIG. 7 illustrates a flowchart 700 high-level view of the system for determining the DAP during imaging according to a preferred embodiment of the present invention. First, at step 710, a general parameter space is synthesized as discussed above. That is, ranges of imaging parameter sets are applied to the imaging system and the resultant DAP for the parameter sets is determined and stored. Next, at step 720, the general parameter space is calibrated to a specific X-ray system. As mentioned above, additional measurements of the DAP at several previous parameter sets are conducted. The DAP measurements are compared to the general parameter space and the general parameter space is adjusted to reflect any system-specific differences. Later, at step 730, when the imaging device is applied to perform clinical imaging, the clinical imaging parameters are applied to the calibrated parameter space. Applying the clinical imaging parameters allows the determination of the DAP during imaging directly. Extraneous measuring equipment for measuring the DAP during imaging may be removed.

As further described below, a preferred embodiment provides a calibrated, software based system for determining the DAP in real time, without external measurement during clinical imaging. A preferred embodiment of the present invention thus allows the elimination of the ion chamber and its associated instrumentation.

As further described below, a preferred embodiment of the present invention first contours a generalized three dimensional parameter space involving the applied X-ray tube voltage in kV, the iris diameter, and the shutter lateral position. The parameter space is preferably normalized to an X-ray tube current of 1 mA so that it may be easily scaled to any applied tube current. An additional parameter space describing the variance of system parameters with regard to shutter rotation may also be constructed for systems employing a rotatable shutter. Next, the three dimensional parameter space, and the shutter rotation parameter space if needed, may be calibrated for use in a specific imaging system. Once the parameter space has been calibrated for use with a specific imaging system, the DAP may be directly determined by applying the current imaging parameters to the parameter space. Typically, this entails a multidimensional interpolation to arrive at a close approximation of the actual DAP for a desired kV, iris position and shutter position.

Consequently, a preferred embodiment of the present invention provides a system for determining the DAP by calculation, thus determining a Calculated Dose Area product (CDAP), without the need to measure the X-ray source using added components such as the above described ion chamber and instrumentation. The CDAP represents a considerably more cost effective solution than the ion chamber and its associated instrumentation. Also, the CDAP may be a more accurate measurement because the DAP measurement errors related to and patient backscatter are minimized due to the absence of the ion chamber at the X-ray source.

As an example, both the three dimensional parameter space and the rotational parameter space may be conceptualized as Look Up Tables (LUTs). The first LUT may be generally denoted as the kV LUT. The kV LUT expresses the topography of the tube voltage, iris diameter, and shutter position parameter space in machine-accessible form. The second LUT may be generally denoted as the rotation LUT. The rotation LUT expresses the topography of the shutter position and the iris diameter in machine-accessible form.

Referring to FIG. 1, to populate the kV LUT, the ion chamber 125 is placed in the path of the X-ray beam. The ion chamber 125 is placed as far away from the X-ray source as possible to reduce off-axis scatter, but still close enough to capture the entire X-ray beam, potential scatter sources, such as the image intensifier input surface, are preferably blocked with lead to reduce X-ray back-scatter. The reduction of X-ray backscatter may yield a more accurate DAP measurement, as described above.

Next, the X-ray tube 110 is energized for a predetermined range and number of X-ray tube voltages, or kV settings. At each kV setting, the dosimeter 130 measures the dose rate at 1 mA. Also, for each kV setting, the iris diameter and shutter leaves position are varied over their ranges in a systematic way, thus providing an array of dose rate data. Next, the dosimeter's ion chamber 125 is placed further away, preferably at the image intensifier plane. The image intensifier surface has been blocked with lead to reduce backscatter, as described above. With the dosimeter positioned at the image intensifier plane, the dose rate is measured at the maximal iris diameter and the shutter leaves fully open. The dose rate is measured at each of the kV settings employed at the previous dosimeter position.

Figure 8:
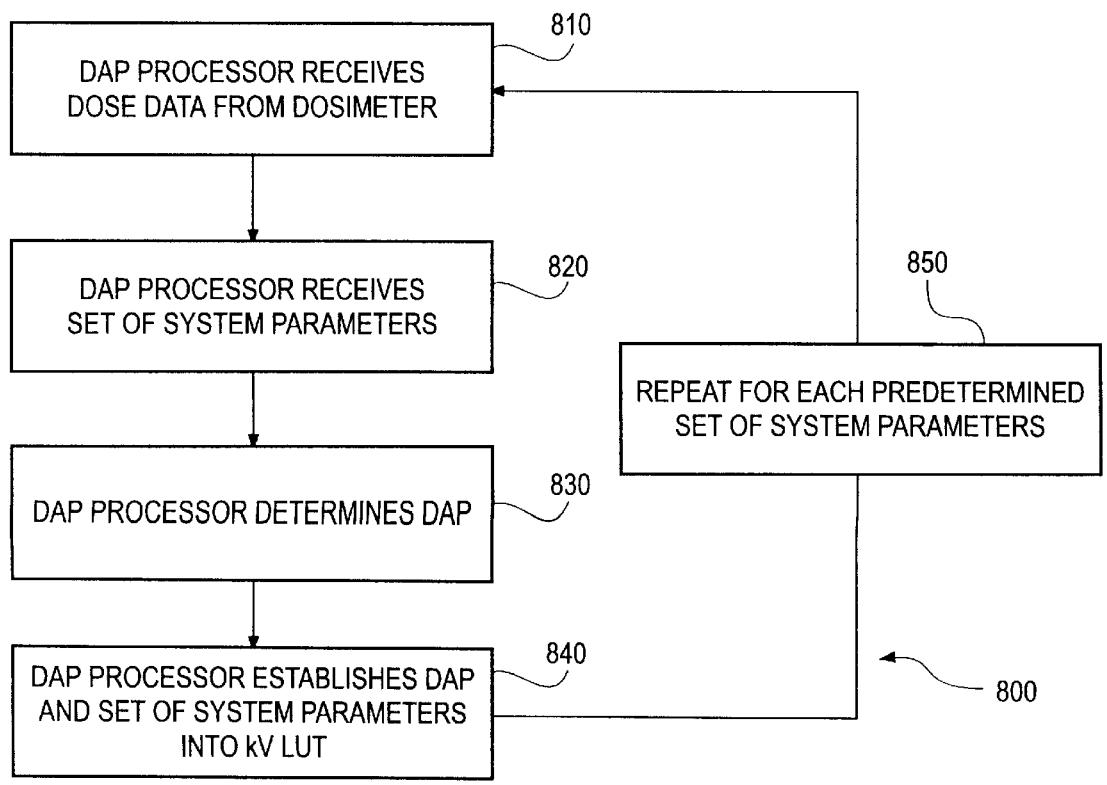
FIG. 8 illustrates a simplified flowchart of the establishment of the kV LUT according to a preferred embodiment of the present invention.

FIG. 8 illustrates a flowchart 800 of the establishment of the kV LUT according to a preferred embodiment of the present invention. First, at step 810, the DAP processor 150 of FIG. 1 receives dose data from the dosimeter 130. Next, at step 820, the DAP processor 150 receives the set of system parameters from the system computer 140 for the X-ray exposure detected by the dosimeter 125. The DAP processor 150 then determines the DAP for the exposure at step 830. Next, at step 840, the DAP processor 150 establishes the determined DAP and the set of system parameters into the parameter space or look up table. At step 850, steps 810–840 are repeated for each predetermined set of system parameters to complete the parameter space.

At the image intensifier plane, the X-ray beam may be larger in cross sectional area than the dosimeter. Additionally, the X-ray beam may vary somewhat in intensity because of the heel effect. Consequently, the dosimeter positioning is preferably optimized so that the dose rate reading is representative of the entire average X-ray beam at this image intensifier plane. The cross-sectional area of the Xray beam at the image intensifier plane may be directly measured, for example, by exposing film. Once the cross-sectional area and the dose rate at the image plane have been determined, they may be synthesized with the dose rate that was measured with the dosimeter positioned closer to the X-ray source to form calibration constants. That is, the cross-sectional area and dose rate at the image intensifier plane and the dose rate at the closer location, holding the other parameters the same (e.g., the iris and shutters fully open in both locations), a calibration constant may be derived based on the ratio of the two measurements. The calibration constant may then be determined for each kV setting. Once derived, the calibration constant may be expanded to determine a DAP value for all settings of iris diameter and shutter position. The calibration constants may be expanded for each of the earlier dose rate measurements made at the closer position to the X-ray source, by multiplying the kV-indexed calibration ratio by the earlier measurements.

During clinical operation, when the operating point input parameters are in between the known parameters of the kV LUT the values of the kV LUT may be interpolated to determine the DAP for the clinical operating parameters. For example, a linear interpolation process may be used to calculate the corresponding output values, as described below. Although the linear interpolation described below is preferred, other interpolation schemes could be used, other than the one described.

Figure 4:
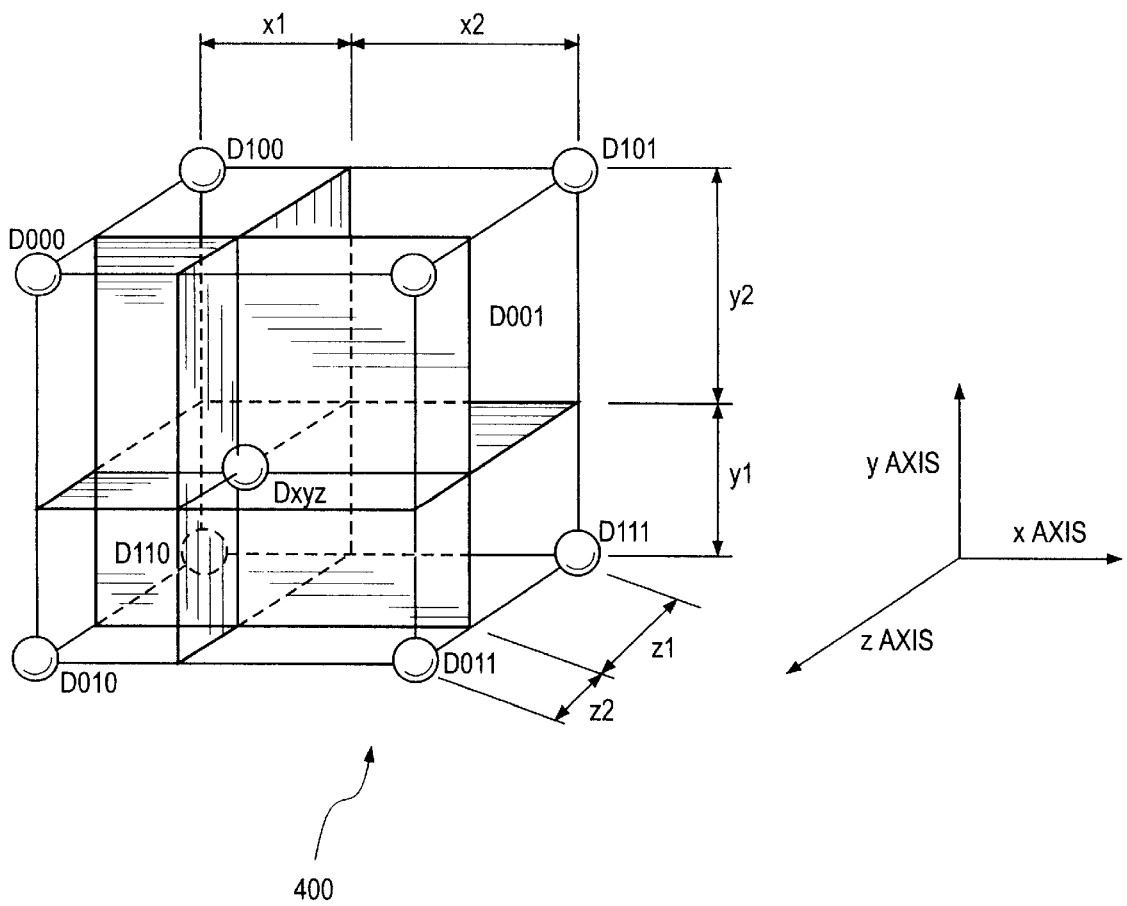
FIG. 4 illustrates the linear interpolation system for determination of the DAP for clinical operating parameters according to a preferred embodiment of the present invention.

FIG. 4 illustrates the linear interpolation system 400 for determination of the DAP for clinical operating parameters according to a preferred embodiment of the present invention. The interpolation system 400 is expressed as a Cartesian coordinate system wherein the axes are oriented as shown in FIG. 4. That is, the positive y axis goes up, the positive x axis goes to the right, and the positive z axis comes out of the plane. The example below encompasses an imaging system having a shutter including two leaves. Different values may result for a single-leaf system, but the general interpolation system remains similar.

In this exemplary three dimensional model, the x-axis represents the iris diameter, the y-axis represent the distance between shutter leaves, and the z-axis represents the applied high voltage kV. As mentioned above, the kV LUT is organized to contain values of dose rate times area, normalized to 1 mA of tube current, for certain values of known X, Y, and Z. The kV LUT is not continuous and often clinical operating parameters may not correspond to the X, Y, and Z values includes in the kV LUT. Consequently, interpolation is preferred to establish the DAP values for the clinical parameters.

For example, a clinical DAP, for certain clinical values of iris diameter, shutter separation, and kV, may be described using the notation Dxyz. If the clinical X, Y, and Z are values that do not happen to correspond to the discrete values in the kV LUT, then the value for Dxyz may be determined by interpolating the closest discrete values to the clinical values. Preferably, the interpolation is a linear interpolation involving the eight closest discrete values to Dxyz. As shown in FIG. 4, these values may be described using the notation D000, D001, D010, D011, D100, D101, D110, and D111. Normalized values representing the "distance" from the eight closest discrete values to the clinical parameter set for Dxyz are then determined. These normalized values are represented in FIG. 4, as x1, x2, y1, y2, z1, and z2. The value of the clinical DAP may then be interpolated as:

$$Dxyz=D000*z2*y2*x1+D001*z2*y2*x2+D010*z2*y1*x1+ \\ D011*z2*y1*x2+D100*z1*y2*x1+D101*z1*y2*x2+ \\ D110*z1*y1*x1+D111*z1*y1*x2$$

Consequently, the DAP for clinical operation may be determined based on the predetermined DAP values of the kV LUT.

Figure 6:
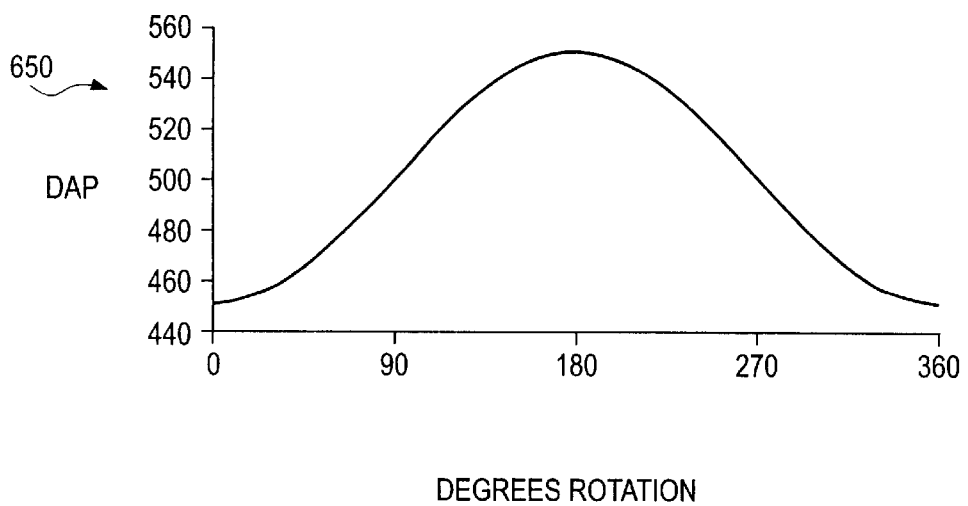
FIG. 6 illustrates the effect of shutter rotation in a single-leaf system for use in determining a preferred embodiment of the present invention.
Figure 6:
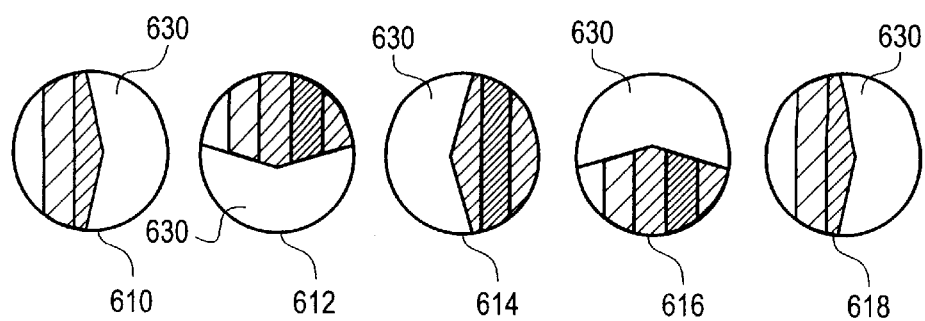

FIG. 6 illustrates the effect of shutter rotation in a single-leaf system. FIG. 6 includes a number of X-ray beam intensity patterns 610–618 and a chart 650. Each of the intensity patterns corresponds to a different rotational angle for the shutter 630 including 0, 90, 180, 270, and 360 degrees as shown. Each of the intensity patterns 610–618 also illustrates the relative positions of the heel effect intensity variance to the shutter 630. As shown in FIG. 6, the rotation of the shutter 630 may alter the intensity of the X-ray beam because the shutter may be attenuating portions of the X-ray beam of greater or lesser intensity, thus altering the overall intensity of the X-ray beam. Altering the overall intensity of the X-ray beam also alters the DAP for the X-ray beam as well, as shown in the chart 650. As shown in FIG. 6, the intensity of the X-ray beam is least when the shutter is oriented at an angle of zero degrees and is maximal when the shutter is oriented at an angle of 180 degrees.

Consequently, if an imaging system employs a shutter having an asymmetrical arrangement for the shutter leaves, such as a single shutter leaf, a rotational LUT related to the rotation of the shutter and the iris position is preferably formed. The employment of the rotational LUT may increase the accuracy of the DAP determination because the asymmetrical arrangement of the shutter leaves may create deviations from the average beam intensity. The employment of the rotational LUT compensates for the deviations from the average beam intensity generated by the asymmetrical shutter leaves. For example, in the single-leaf shutter case, the heel effect has the greatest influence when the iris is fully open and the shutter is closest to the central axis (most closed). As the iris diameter and position of the shutter change, the X-ray beam pattern introduced by the heel effect may change substantially. As the X-ray beam pattern changes, the DAP may change as well.

For example, in the case of a single leaf shutter, the rotational LUT, varies with iris diameter and shutter position, may be determined as follows. As described above, the kV LUT measurements are performed with the shutter leaf positioned at 90 degrees. The rotational LUT may be expressed as:

$$A_{I,S} = DAP_{angle\ 180\ deg}/[DAP_{from\ kv\ LUT}] - 1 = DAP_{angle\ 180\ deg}/[(DAP_{angle\ 0\ deg} + DAP_{angle\ 180\ deg})/2] - 1$$

That is, the rotational LUT, $A_{I,S}$, corresponds to various values of the iris diameter, I, and the shutter position, S. For each value of the iris diameter and the shutter position, the DAP from the kV LUT (at 90 degrees shutter leaf) and a new DAP determined with the shutter leaf positioned at 180 degrees are synthesized to determine the corresponding value for the rotational LUT. Alternatively, data from the kV LUT, may be used with the average of the shutter leaf at angles of zero and 180 degrees which typically is equivalent to the shutter leaf at 90 degrees.

Once the rotational LUT has been determined, it may be applied to clinical parameters to determine a corrected DAP for the clinical parameters. The rotational LUT may be employed to find the DAP at any angle as follows:

$$DAP_{at\ angle\ \theta} = DAP_{interpolated\ from\ kVLUT} * [1 - A_{I,S} * \cos(\theta)]$$

where $A_{I,S}$ corresponds to the values contained in the rotational LUT that vary with iris (I) and shutter (S) positions, and $\theta$ is the angle of rotation, as described above and in FIGS. 2 and 3.

Once the kV LUT and the rotational LUT have been determined for a specific line of X-ray systems, the LUTs are preferably further optimized for each individual X-ray imaging system. That is, any differences between X-ray tubes may be analyzed and reflected in system-specific LUTs in order to provide the most accurate DAP. The calibration of the kV LUT and rotational LUT for specific, individual x-ray tubes is further set forth below.

First, with the iris and shutter fully away from the central axis (fully open), a number (preferably 6) of X-ray shots are taken and the DAP measurements recorded with a dosimeter. The X-ray shots are preferably taken over the spectrum of kV range for the system. The kV range is typically from 40 kV to 120 kV. Preferably, the six values are chosen to be closer together in the lower portion of the kV range and farther apart in the higher portion of the kV range. The kV values are preferably closer together in the lower portion of the kV range because of a greater sensitivity to errors in the DAP measurement in the low kV range.

Once the X-ray shots have been taken, the DAP values for the shots are fit to a curve. The curve is then used to modify the values of the kV LUT to adapt the LUT to the DAP values for the individual X-ray tube. Preferably, an over-specified least squares fit to a quadratic polynomial (or some other higher-order polynomial) is used to determine the optimal curve that represents the acquired dose rate data through the measured points. Correction constants for the kV LUT may be found by calculating the ratio between values from the least squares fit and the originally measured data from the dosimeter, used to calculate the original kV LUT. The correction constants are then used to change the output values in the kV LUT. In this fashion, all values (including when the iris and shutter leaves are not fully open) can be proportionally altered by the correction constants for each kV.

Mathematically, the correction constant may be expressed as:

$$y = [A(kV)^2 + B(kV) + C]$$

where y is the best least-squares fit for the dose rate and A, B, and C are constants to be determined. To solve for A, B, and C, first define the following matricies $\Omega$, $\Phi$, $\Psi$:

$$\Psi = \begin{vmatrix} y1 \\ y2 \\ y3 \\ y4 \\ y5 \\ y6 \end{vmatrix} \quad \Omega = \begin{vmatrix} C \\ B \\ A \end{vmatrix} \quad \Phi = \begin{vmatrix} 1 & kV_1 & (kV_1)^2 \\ 1 & kV_2 & (kV_2)^2 \\ 1 & kV_3 & (kV_3)^2 \\ 1 & kV_4 & (kV_4)^2 \\ 1 & kV_5 & (kV_5)^2 \\ 1 & kV_6 & (kV_6)^2 \end{vmatrix}$$

Where $\Psi$ represents the six X-ray shots y1 to y6, $\Omega$ represents the constants to be solved for, and $\Psi$ represents the voltages of the six X-ray shots. The constants may now be directly solved as follows:

$$\Omega = (\Phi^T \Phi)^{-1} \Phi^T \Psi$$

Finally, the kV LUT may be corrected as:

$$DAP_{corrected\ kVLUT} = DAP_{original\ kVLUT} * (y/y_o)$$

where $y_o$ is the originally measured data from the dosimeter that was used to calculate the original kV LUT.

In addition to the kV LUT being calibrated to the individual X-ray tube, the rotational LUT is preferably calibrated to the individual X-ray tube. The rotational LUT calibration may be used to correct for variations in heel effect in each specific tube, over the rotation range of the single shutter leaf, for example. (As mentioned above, the rotational LUT is employed for those systems having asymmetric shutters, such as single shutter leaf systems.)

First, the dose rates at angles of both $\theta = 0$ and 180 degrees of shutter leaf angle are determined. The dose rate determination is repeated for the various values of iris diameter used in the rotational LUT. The dose rates for the various iris diameter values are then grouped into two arrays, $D_{0deg}$, and $D_{180deg}$.

Next, a new array $D_M$ is constructed including the two arrays, $D_{0deg}$ and $D_{180deg}$.

$$D_M = D_{180\ deg}/[(D_{0\ deg} + D_{180\ deg})/2] - 1$$

The values in the rotational LUT for the same iris settings as above, and the shutter fully closed are denoted as an array $D_T$. Then a correction array, $D_C$, is computed by dividing each value in the $D_M$ array by each respective value in the $D_T$ array. Multiplying the rotational LUT by the correction array $D_C$ yields the corrected rotational LUT. This may be expressed mathematically as:

$$A_{I,S\ corrected} = A * D_C = A * D_M / D_T$$

Finally, a fully corrected DAP value from both the kV LUT and the corrected Rotation LUT may be determined as follows:

$$DAP_{fully\ corrected\ at\ angle\ \theta} = DAP_{interpolated\ from\ corrected\ kVLUT} * [1 - A_{I,S\ corrected} * \cos(\theta)]$$

As described above, if the clinical imaging system does not use an asymmetric shutter such as a single leaf shutter, then the last, bracketed term would be absent because a rotational LUT need not be applied.

FIG. 9 illustrates a flowchart 900 providing a lower-level view of the system for determining the DAP during clinical imaging of FIG. 7. First, at step 910, the kV LUT is constructed. The kV LUT is typically composed of the DAP for a parameter set of the X-ray tube voltage, iris diameter, and shutter position. Next, at step 920, if the shutter is asymmetric, a rotational LUT is constructed. As described above, the rotational LUT is typically composed of the change in DAP with regard to shutter rotation angle. Now that generalized parameters for the DAP may be determined, in order to construct a more accurate model, the LUTs are calibrated to a specific X-ray tube. Thus, at step 930, the kV LUT is calibrated to a specific imaging system. As described above, a number of DAP values at different tube voltages may be determined. The system's tube voltages may be curve-fitted as described above. The resulting curve may be employed to alter the kV LUT to reflect the specific characteristics of the individual imaging system. Also, in much the same fashion, the rotational LUT may be calibrated to the specific imaging system at step 940. Finally, at step 950, the imaging system is ready to be used in clinical imaging. During clinical imaging, the parameter set employed by the imaging system is applied to the system-calibrated kV LUT to determine the DAP for the parameter set being used. If the clinical imaging system employs an asymmetric shutter, the shutter angle may be applied to the system-calibrated rotational LUT to determine a scale factor for the DAP determined through the kV LUT One of the primary advantages of the preferred system for determining DAP is its lower cost. That is, the components to obtain the data for the calculation process are typically less expensive than the components needed to directly measure DAP using prior technology. The system for determination of the DAP may be applied in both stationary (fixed-room) and mobile X-ray imaging systems. For example, in higher performance mobile fluoroscopic X-ray imaging systems, the components needed for the preferred embodiment are likely to already exist in their entirety in order to accomplish other desired purposes. If the components already exist, only added software may be required and no added part costs may be incurred. Additionally, manufacturing flexibility may be improved because the preferred embodiment may easily be enabled and a calibration procedure performed without the need for any further parts. Also, with sufficiently sophisticated algorithms and precise components, the preferred embodiment may yield a more accurate DAP determination than the earlier DAP determination method. This is because the earlier DAP determination was subject to the off axis scatter and patient back scatter errors mentioned discussed above.

The preferred embodiment provides a system for determining a calculated Dose Area Product without the need to use specially dedicated components for direct measurement of the X-ray radiation during clinical use. Additionally, the present system also accommodate non-trivial X-ray beam radiation profiles such as those created by semi-transparent and tapered beam filters, for example, shutter leaves with tapered thickness, irregular width shapes (such as a crescent) that vary in position and angle with user selection, and X-ray tube heel effect. Also, calibration of the present system enhances the accuracy of the resulting DAP by tailoring the determination to individual X-ray tubes.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope.

Therefore, it is intended that the invention not be limited to the particular embodiment disclosed, but that the invention will include all embodiments falling within the scope of the appended claims.

What is claimed is:

1. A system for determining the Dose Area Product (DAP) for an X-ray imaging system during clinical imaging, said system including:
    at least one pre-determined parameter space composed of a DAP contour over ranges of imaging parameters; and
    a DAP processor receiving a set of the current imaging parameters for said X-ray imaging system and applying said set to said parameter space to determine the DAP for the X-ray system.

2. The system of claim 1 wherein said pre-determined parameter space is a calibrated parameter space calibrated to said X-ray imaging system.

3. The system of claim 1 wherein said parameter space is a Look Up Table (LUT).

4. The system of claim 3 wherein said LUT includes parameters for at least one of X-ray tube voltage, iris diameter, and shutter position.

5. The system of claim 1 further including a rotational parameter space corresponding to the change in DAP with rotation of the shutter.

6. The system of claim 5 wherein said rotational parameter space is calibrated to the characteristics of said specific X-ray system to form a calibrated rotational parameter space.

7. The system of claim 6 wherein said DAP processor applies the rotation of the shutter to the calibrated rotational parameter space to determine a rotational correction for said DAP.

8. The system of claim 7 wherein said DAP applies said rotational correction to said DAP to determine the DAP for the clinical imaging system.

9. The system of claim 5 wherein said rotational parameter space is a Look Up Table.

10. A method for determining the Dose Area Product (DAP) for an X-ray imaging system during clinical imaging, said method comprising the steps of:
    synthesizing a general parameter space composed of a DAP contour over ranges of sets of imaging parameters;
    calibrating said general parameter space to the characteristics of a specific X-ray system to form a calibrated parameter space; and
    applying a set of imaging parameters from said X-ray imaging system during clinical imaging to said calibrated parameter space to determine the DAP.

11. The method of claim 10 wherein said general parameter space is a Look Up Table (LUT).

12. The method of claim 11 wherein said LUT includes a parameters for at least one of X-ray tube voltage, iris diameter, and shutter position.

13. The method of claim 10 further including synthesizing a rotational parameter space corresponding to the change in DAP with rotation of the shutter.

14. The method of claim 13 further including calibrating said rotational parameter space to the characteristics of said specific X-ray system to form a calibrated rotational parameter space.

15. The method of claim 14 further including applying the rotation of the shutter to the calibrated rotational parameter space to determine a rotational correction for said DAP.

16. A system for constructing a multi-dimensional parameter space for use in determining the Dose Area Product (DAP) for an X-ray imaging system during clinical imaging, said system including:

an X-ray imaging system, said X-ray system being energized a plurality of times with at least one varying set of imaging parameters;

a dosimeter for determining dose data for said X-ray system for a particular set of imaging parameters; and a DAP processor receiving said dose data from said dosimeter and receiving said set of imaging parameters from said X-ray imaging system, said DAP processor determining the DAP and establishing the DAP and the set of imaging parameters in a memory indexable by at least one of said imaging parameters.

17. The system of claim 16 wherein a set of imaging parameters includes at least one of X-ray tube voltage, iris diameter, and shutter position.

18. The system of claim 16 wherein said parameter space is calibrated to a specific X-ray system.

* * * * *